(12) United States Patent
Lawson et al.

(10) Patent No.: US 9,261,407 B2
(45) Date of Patent: *Feb. 16, 2016

(54) THERMOMETER FOR DETERMINING THE TEMPERATURE OF AN ANIMAL'S EAR DRUM AND METHOD OF USING THE SAME

(76) Inventors: Eric M. Lawson, Auburn, NY (US); David M. Antos, Constantia, NY (US); Matthew J. Kinsley, Liverpool, NY (US); John A. Lane, Weedsport, NY (US); Scott A. Martin, Warners, NY (US); Matthew D. Mullin, Memphis, NY (US); David E. Quinn, Auburn, NY (US)

( * ) Notice: Subject to any disclaimer, the term of this patent is extended or adjusted under 35 U.S.C. 154(b) by 399 days.

This patent is subject to a terminal disclaimer.

(21) Appl. No.: 12/859,611

(22) Filed: Aug. 19, 2010

(65) Prior Publication Data

US 2011/0105910 A1    May 5, 2011

Related U.S. Application Data

(63) Continuation-in-part of application No. 12/610,760, filed on Nov. 2, 2009, now Pat. No. 8,306,774.

(51) Int. Cl.
*A61B 6/00* (2006.01)
*G01J 5/00* (2006.01)
(Continued)

(52) U.S. Cl.
CPC ............. *G01J 5/0003* (2013.01); *G01J 5/0011* (2013.01); *G01J 5/02* (2013.01); *G01J 5/0275* (2013.01); *G01J 5/04* (2013.01); *G01J 5/048* (2013.01); *G01J 5/08* (2013.01); *G01J 5/0846* (2013.01)

(58) Field of Classification Search
CPC ...... A61B 5/6815; A61B 5/6817; A61B 5/01; A61B 1/227; A61B 2562/02; A61B 5/0008; A61B 5/0478; A61B 5/6816; A61B 2562/0257; A61B 2562/247; G01J 5/0011; G01J 2005/0081; G01J 5/522; A61N 1/36032
USPC ............................ 374/121; 600/474; 702/135
See application file for complete search history.

(56) References Cited

U.S. PATENT DOCUMENTS 3,373,611 A    3/1968    Trott
4,521,772 A    6/1985    Lyon
(Continued)

FOREIGN PATENT DOCUMENTS

CN           101542423 A    9/2009
DE      20 2004 003021       5/2004
(Continued)

OTHER PUBLICATIONS

Notification of Transmittal of The International Search Report and The Written Opinion of the International Searching Authority, or The Declaration; 11 pages; Jul. 8, 2011.
(Continued)

*Primary Examiner* — Long V Le
*Assistant Examiner* — Ellsworth Weatherby

(57) ABSTRACT

The present invention relates to a thermometer for determining the temperature of an animal's ear drum. The thermometer includes a probe, an infrared-radiation detector adapted to receive infrared radiation emitted by the ear drum, and devices that help determine the probe's position in the ear canal so as to optimize the infrared radiation received from the ear drum, and to minimize the infrared radiation received from other ear parts. A method of using the thermometer is also disclosed.

11 Claims, 14 Drawing Sheets

(51) Int. Cl.
*G01J 5/02* (2006.01)
*G01J 5/04* (2006.01)
*G01J 5/08* (2006.01)

(56) References Cited

U.S. PATENT DOCUMENTS

| | | | |
|---|---|---|---|
| 4,521,773 | A | 6/1985 | Lyon |
| 4,706,682 | A * | 11/1987 | Stypulkowski et al. ...... 600/379 |
| 4,737,038 | A | 4/1988 | Dostoomian |
| 4,861,168 | A | 8/1989 | Ziegler et al. |
| 5,179,951 | A * | 1/1993 | Knudson ...................... 600/310 |
| 6,030,117 | A | 2/2000 | Cheslock et al. |
| 6,272,375 | B1 | 8/2001 | Katzir et al. |
| 6,358,216 | B1 * | 3/2002 | Kraus et al. ................... 600/549 |
| 6,626,568 | B2 | 9/2003 | Sato et al. |
| 7,314,310 | B2 | 1/2008 | Medero |
| 7,434,992 | B2 | 10/2008 | Tabata et al. |
| 7,484,884 | B2 | 2/2009 | Lane et al. |
| 2002/0143257 | A1 * | 10/2002 | Newman et al. .............. 600/474 |
| 2002/0193703 | A1 | 12/2002 | Sato et al. |
| 2004/0170216 | A1 | 9/2004 | Russak et al. |
| 2004/0233968 | A1 * | 11/2004 | Tabata et al. .................. 374/121 |
| 2005/0002437 | A1 | 1/2005 | Fraden |
| 2005/0010273 | A1 * | 1/2005 | Walker et al. ................. 607/105 |
| 2005/0094705 | A1 | 5/2005 | Chi |
| 2005/0249263 | A1 | 11/2005 | Yerlikaya et al. |
| 2006/0217632 | A1 * | 9/2006 | Causevic et al. .............. 600/559 |
| 2006/0287689 | A1 * | 12/2006 | Debruyne et al. ............. 607/57 |
| 2007/0047618 | A1 | 3/2007 | Howanski |
| 2007/0055171 | A1 | 3/2007 | Fraden |
| 2007/0085686 | A1 * | 4/2007 | Oz ............................ 340/572.8 |
| 2007/0242726 | A1 * | 10/2007 | Medero ......................... 374/164 |
| 2008/0107152 | A1 | 5/2008 | Ishimaru et al. |
| 2008/0192961 | A1 * | 8/2008 | Radivojevic et al. ......... 381/151 |
| 2009/0182526 | A1 | 7/2009 | Quinn et al. |
| 2009/0252386 | A1 * | 10/2009 | Dean et al. .................... 382/124 |
| 2010/0160763 | A1 * | 6/2010 | Tsai et al. ..................... 600/393 |
| 2011/0216806 | A1 | 9/2011 | Weng |
| 2012/0177083 | A1 * | 7/2012 | Lin et al. ....................... 374/121 |

FOREIGN PATENT DOCUMENTS

| | | |
|---|---|---|
| EP | 1030316 A1 * | 8/2000 |
| JP | 2000005137 A | 1/2000 |
| JP | 2005-224617 | 8/2005 |
| WO | WO 2009/041912 A1 | 4/2009 |
| WO | 2011113727 A1 | 9/2011 |

OTHER PUBLICATIONS

Search History, 5 pages, Jul. 8, 2011.
Tyco/Healthcare; Kendall GENIUS 2 Infrared Tympanic Electronic Thermometer; 2006; pp. 1-13; Tyco Healthcare Group LP; USA.
Notification of Transmittal of The International Search Report and The Written Opinion of the International Searching Authority, or The Declaration; 8 pages; May 26, 2011.
Anal Probe with Adjustable Depth, by ArtraMaples88 on Oct. 18, 2011, From gerd.goohealthlife.com; last viewed Feb. 8, 2012.
Vicks Baby Rectal Thermometer, Source: http://www.amazon.com/Vicks-V934-Baby-Rectal-Thermometer/dp/B0002AHVZU; last viewed Feb. 8, 2012.
Ultrasound Rectal Probe R7.5 Source: http://www.alibaba.com/product-gs/490643023/ultrasound_rectal_probe_R7_5.html; last viewed Feb. 8, 2012.
Supplementary European Search Report, Oct. 11, 2013, 7 pages.
Informal, uncertified, "Google translate" translation, Dec. 12, 2013, 5 pages.
Australian Patent Examination Report No. 1, Jul. 15, 2013, 4 pages.
Uncertified Google Translation of the Chinese Patent Application No. CN101542423A, Sep. 23, 2009, 19 pages.

* cited by examiner ized by reuse, various factors# THERMOMETER FOR DETERMINING THE TEMPERATURE OF AN ANIMAL'S EAR DRUM AND METHOD OF USING THE SAME

CROSS-REFERENCE TO RELATED APPLICATIONS

The present application is a continuation-in-pan patent application of, and claims priority to and the benefit of, U.S. patent application Ser. No. 12/610,760, filed Nov. 2, 2009 entitled "THERMOMETER FOR DETERMINING THE TEMPERATURE OF AN ANIMAL'S EAR DRUM AND METHOD OF USING THE SAME", which is hereby incorporated by reference in its entirety.

FIELD OF INVENTION

The present invention relates to a thermometer for determining the temperature of an animal's ear drum and a method of using such thermometer. The thermometer senses infrared radiation emitted by the ear drum and the amount of infrared radiation detected is correlated with an associated temperature. The thermometer may include various devices for measuring the thermometer position with respect to the ear canal so that an accurate reading of the temperature of the ear drum may be obtained.

BACKGROUND OF THE INVENTION

The core body temperature is the operating temperature of an organism in deep structures of the body such as the liver, in contrast to temperatures of peripheral tissues such as the organism's skin. The core body temperature of a warm-blooded animal such as a human is usually a strong indicator of the state of the animal's health. For example, the condition of a high temperature is often caused by an infectious disease, and similarly, a high temperature may also indicate that the animal is suffering from a heat stroke. Such conditions, if not treated properly and quickly, may lead to more serious medical conditions and can result in a fatality.

While it is known that the core body temperature of a human tends to have the lowest value in the second half of the sleep cycle and that a human's body temperature typically changes by about 0.5 degrees Celsius (0.9 degrees Fahrenheit) between its highest and lowest points each day, it is important to monitor frequently any significant trends in the individual's core body temperature, such as to assess whether a particular medical treatment is working sufficiently quickly and favorably.

Typically, there have been four methods of trying to obtain the core body temperature of a warm-blooded animal such as a human. First, an oral thermometer may be placed in the mouth. Temperatures taken by this method, however, may be influenced by drinking, eating, or breathing. A second method is to take the temperature of the animal's underarm. Unfortunately, the temperature of the underarm may be vastly different from the core body temperature because the thermometer is placed next to the skin, which is a tool the body uses to control core body temperature. Moreover, skin temperatures are often influenced by factors such as medication, clothing, and external temperature. A third method has been the use of rectal thermometers. Such thermometers are not conveniently administered, often pose psychological discomfort, and present a contamination risk. The fourth method is the use of ear thermometers that measure the temperature of the tympanic membrane a/k/a the ear drum. Such ear thermometers typically involve detecting infrared radiation emitted from the ear drum.

Infrared thermometry is based upon the principle that all material emits electromagnetic radiation as so-called "blackbody" radiation. The emission spectrum, that is, the intensity of the radiation at each wavelength in a continuum of wavelengths, is in accord with Plank's law. For materials at about 60 degrees F. to 100 degrees F., their emission spectra tend to peak in the mid-infrared range, at wavelengths around 10 microns. The intensity of emission is proportional to temperature, and therefore, the temperature of a material can be determined by measuring its infrared emission. Such infrared radiation can be detected by any one of a number of different types of sensors such as thermopiles, pyroelectric sensors, and other types of infrared sensors.

An infrared ear thermometer can be used quickly and easily in a hospital or at home, is not embarrassing to use, and avoids contamination from reuse. Nevertheless, various factors can significantly affect the accuracy of temperature readings obtained by detecting infrared radiation emitted from the ear drum. For example, temperature readings can be affected by a relatively cold outer ear or ear canal, a hairy ear canal, or the presence of possible disease or infection. Moreover, due to variations in physical attributes of ear canal geometry or a defective positioning technique, the temperature readings may be skewed.

The present invention helps insure that the infrared radiation probe inserted into the ear canal is pushed deep enough into the ear canal so as to minimize the effects of the outer ear and ear canal temperature, to minimize the affect of physical contours of and hair within the ear canal, and to direct the probe toward the ear drum, without contacting the ear drum.

SUMMARY OF THE INVENTION

The present invention relates to a thermometer for determining the temperature of an animal's ear drum. The thermometer includes a probe, an infrared-radiation detector adapted to receive infrared radiation emitted by the ear drum, and devices that help determine the probe's position in the ear canal so as to optimize the infrared radiation received from the ear drum, and to minimize the infrared radiation received from other ear parts. A method of using the thermometer is also disclosed.

BRIEF DESCRIPTION OF THE DRAWINGS

The invention will be described with reference to the accompanying drawings, wherein.

DESCRIPTION OF A PREFERRED EMBODIMENT

Figure 1:
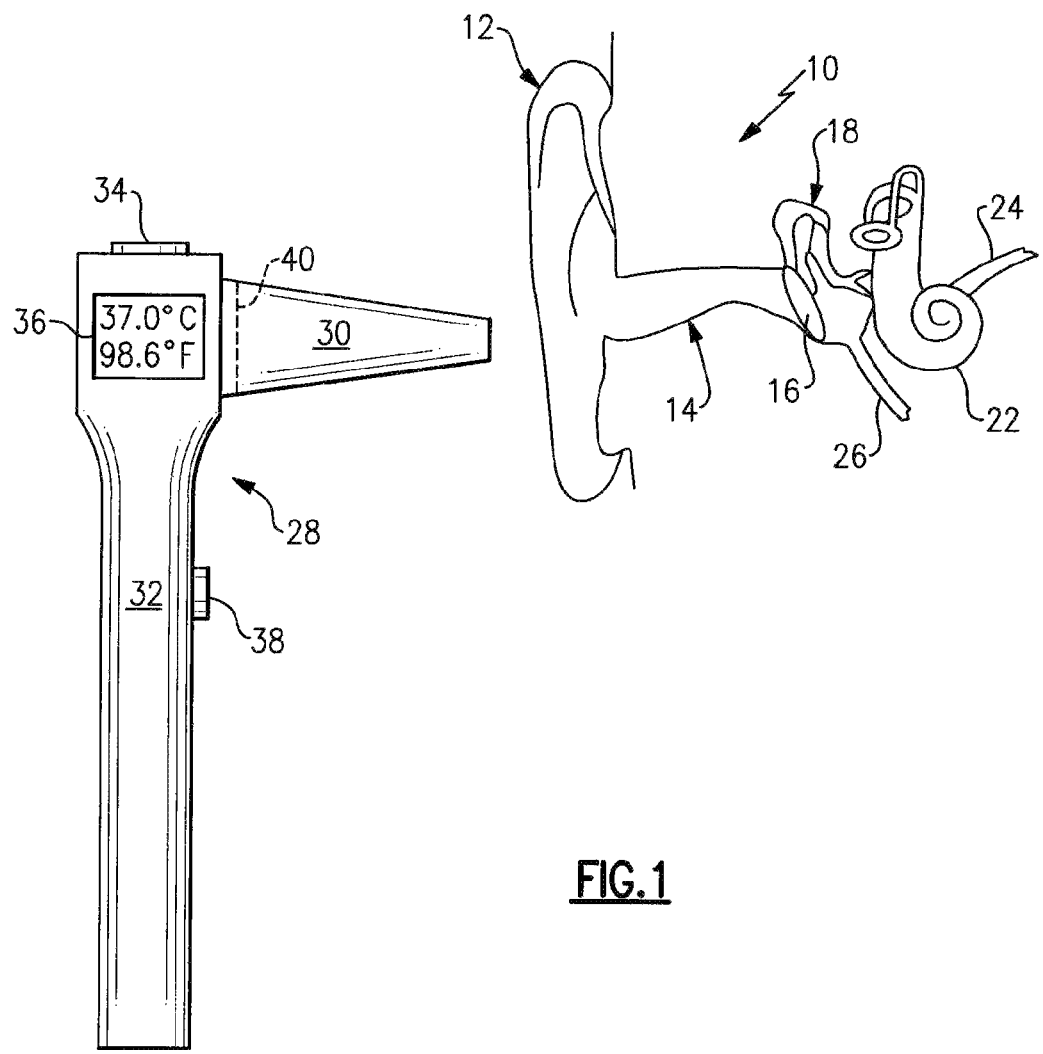
FIG. 1 is a schematic illustration of the principal components of a human's ear along with a plan view of a thermometer constructed in accordance with an embodiment of the present invention.

The present invention will be described with reference to the accompanying drawings wherein like reference numerals refer to the same item. It should be appreciated that the following description is intended to be exemplary only and that the scope of the invention envisions other variations and modifications of these particular exemplary embodiments.

There is shown in FIG. 1, in general illustration, the components of a human ear 10. An outer portion of the ear 10 known as the pinna 12 is formed of cartilage and is adapted to channel sound waves to the so-called ear canal 14, where the vibrations are directed onto the ear drum 16. The vibrations are further transmitted from the ear drum 16 through three tiny bones known as the ossicles 18, commonly known as the hammer, anvil, and stirrup, to the cochlea 22. The auditory nerve 24 connects the cochlea 22 to the brain. The region interior to the ear drum 16 opens to the Eustachian tube 26, which helps to maintain an even air pressure on each side of the ear drum 16.

Figure 2:
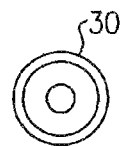
FIG. 2 is a longitudinal end view of a substantially frusto-conical probe that may be used in connection with the present invention.

There shown in FIG. 1 a thermometer 28 that is fashioned generally in the shape of an otoscope, although other configurations are contemplated within the scope of the present invention. The thermometer 28 includes a frusto-conical speculum or probe 30 and a handle section 32 upon which are mounted a top display panel 34, a side display panel 36, and a manually activated push button 38. As will be appreciated from reviewing FIG. 1, the smaller end of the frusto-conical probe 30 is adapted to be inserted relatively deep into the ear canal 14, however, an intermediate section of the probe 30 is adapted to abut the outer-most portion of the ear canal 14 at a point where the smaller end of the probe 30 does not contact the ear drum 16. Probe configurations other than frusto-conical are also contemplated within the scope of the present invention. For example, the probe 30 may be more funnel-shaped with a smaller end that is substantially cylindrical. As shown in FIG. 2, which is an end view of the probe 30, the probe 30 is preferably hollow and possesses a relatively thin wall. As such, the opening in the smaller end of the probe 30 provides an opening through which the infrared radiation emitted by the ear drum 16 may pass through the probe 30 to an infrared detector 40 that may be disposed in the thermometer 28 adjacent to the larger end of the probe 30. As such, the probe 30 can act as an optical waveguide to help transmit infrared radiation emitted by the ear drum 16 onto the infrared-radiation detector 40. Preferably the interior wall of the probe 30 is coated with a material that possesses a high reflectance to infrared radiation. It should be appreciated that within the scope of the present invention, the infrared-radiation detector 40 may be placed at various positions, including most preferably at the smaller end of the probe 30. It is further preferred that the probe 30 be detachable from the handle portion of the thermometer 28 for maintenance and cleaning, or even more preferably, for disposal so as to minimize any contamination problems from re-use. In a preferred embodiment, the thermometer 28 includes a disposable, infrared-transparent sleeve (not shown) configured to conformingly cover the peripheral surface of the probe 30 adapted to be inserted relatively deep into the ear canal. The use of a plurality of such sleeves allows the probe 30 to be re-used by discarding a sleeve after use and replacing the sleeve with a new, unused sleeve.

Prior to use, the thermometer 28 is calibrated so that an object of a known temperature emits radiation onto the infrared-radiation detector 40. The intensity of the infrared radiation detected will be associated with the known temperature of that object. Such calibration can be performed with regard to known temperatures over the normal range of core body temperatures associated with a human or other animal. Thus, the amount of infrared radiation impinging upon the infrared-radiation detector 40 will be correlated with a particular temperature, which may be displayed in both Celsius and Fahrenheit on either the top visual display 34 or the side visual display 36, or both. It should also be appreciated that the thermometer 28 may be provided with a wired or wireless transmitter that provides the correlated temperature to a remote device that monitors, further processes, or records the temperature.

Figure 3:
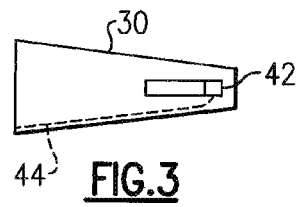
FIG. 3 is a side view illustration of the probe shown in FIG. 2 bearing a sliding movement sensor, such as a component of a conventional optical mouse.

There is shown in FIG. 3 a probe 30 on which is mounted an optical recognition sensor 42, that is common component of an optical mouse. The sensor 42 is preferably placed on the exterior surface of the small end of the probe 30. The sensor 42 may possess a wide range of selected sizes, and may be placed at various regions around the small end of the probe 30, and may continuously extend around the small end of the probe 30.

Optical mice are commonly used for desktop personal computers over a pad or other surfaces to help move and guide a cursor arrow appearing on the computer screen. Early versions of mice utilized a rolling ball. Movement of the ball was translated with the arrow appearing on the computer screen. Later versions have utilized optical mice that often use light-emitting diodes and photo diodes to detect movement relative to the underlying surface, rather than a moving part such as a ball.

One of the early pioneers of optical mice was Richard F. Lyon of Xerox Corporation, and the construction and the operation of his optical mice are described in his U.S. Pat. Nos. 4,521,772 and 4,521,773. Such optical mice work by using an optoelectronic sensor to take successive pictures of the surface on which the mouse operates or views. The optical mice illuminate the surface over which they track, again, using a light-emitting diode or a photo diode, which are photographed and analyzed for optical variances or textures. Changes between one image frame and the next are processed by the image processing part of a computer chip and translated into movement along two axes using an optical flow estimation algorithm. By monitoring the change of position of a pattern, texture, or other feature being photographed, the computer chip can calculate the acceleration, velocity, and position of the mouse relative to the surface being tracked.

In one embodiment of the present invention, the optical sensor 42 tracks only a single point or feature and determines how far the feature has moved relative to the sensor 42, that is, how far the probe 30 is being inserted into the ear canal 14.

In the context of the present invention, the preferred surface being tracked is the peripheral skin surface of the ear canal 14. A thermometer 28 of the present invention, utilizing a sensor 42, is thus capable of continually monitoring the progress of the insertion of the probe 30 into the ear canal 14. As shown in FIG. 3, the sensor 42 may be connected via a wire 44 disposed along either the inner wall, or the outer wall, of the probe 30 to a microprocessor located within the handle 32 of the thermometer 28, which may be programmed to analyze input from the sensor 42 and the infrared detector 40 to determine when the probe 30 and the sensor 42 were at a point of deepest penetration into the ear canal 14, to determine what the intensity of the infrared radiation detected by the infrared sensor 40 was at that time, and to correlate that intensity to a temperature, which may be displayed on either or both of the displays 34, 36.

The optical sensor 42 may utilize a sampling rate of 1,500 frames per second, which is an ample sampling rate to determine the point of farthest penetration. An optical sensor that is believed to be suitable for the foregoing application is made by Agilent, with the model number ADNS-2610.

The manually activated push button 38 may trigger a switch that commences the tracking by the optical mouse 42, which may continue over a fixed duration, such as four seconds. Alternatively, the push buttons 38 might be redepressed to stop the tracking. Also this could be a partially or completely automatic process.

Figure 4:
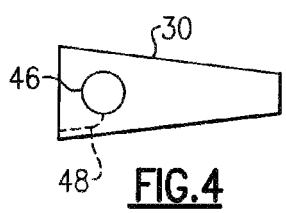
FIG. 4 is a side view illustration of the probe shown in FIG. 2 bearing an accelerometer in accordance with one embodiment of the present invention.

There is shown in FIG. 4 another embodiment of the present invention in which an accelerometer 46 is mounted on the exterior surface of the probe 30, near the large end thereof. As will be appreciated from reading the following description of this embodiment, the accelerometer 46 may be placed almost anywhere along the probe 30, and may even be placed on the handle portion 32 of the thermometer 28 and aligned with the probe 30. The accelerometer 46 may be connected via a wire 48 disposed along either the internal wall or the external wall of the probe 30 to an associated microprocessor disposed within the handle 32.

The accelerometer 46 measures acceleration and deceleration. Typically, the accelerometer 46 includes a mass disposed on a spring, and when the accelerometer (i.e., the mass) is moved, the spring will deflect. Most commonly, the capacitance between a set of fixed beams and a set of beams attached to the mass is measured. Alternatively, piezoresistors may be integrated into the springs to detect spring deformation.

By detecting how and when the spring is deflected, not only the acceleration, but also the speed, tilt and distance in one (axial) direction, two orthogonal directions, or three orthogonal directions, of the mass (i.e., the accelerometer) can be determined relative to a starting point. Deflection of the spring may be measured in either an analog or a digital manner. Other types of accelerometers may also be advantageously employed in the context of the present invention.

Figure 5:
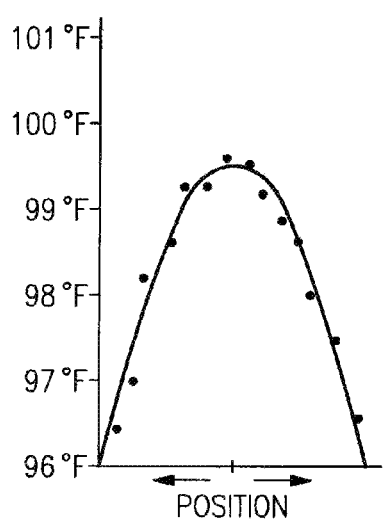
FIG. 5 is a graph of the signal obtained, which may be used to calculate the temperature of the ear drum using the probe shown in FIG. 4.

In the context of the present invention, the thermometer 28 is held such that the probe 30 is disposed only partially into the ear canal 14. The thermometer 28 is moved toward the ear canal 14 such that the probe 30 is inserted farther into the ear canal 14, and thereafter the thermometer 28 is withdrawn away from the ear canal 14. Again, a microprocessor in the handle 32 may receive input from the accelerometer 46 and the infrared-radiation detector 40 to determine when the probe 30 was at its deepest penetration into the ear canal 14 and to determine the intensity of the infrared radiation detected by the detector 40 at that time, which is correlated with a temperature and displayed in one or both of the displays 34, 36. Alternatively the microprocessor might chart the temperature over certain time intervals from the time of ear canal entrance until the thermometer 28 is withdrawn to the same position. An exemplary chart of temperature versus position in the ear canal 14 is depicted in FIG. 5. In order to select the definitive temperature of the ear drum, the microprocessor may be programmed to utilize an algorithm and plot a "best fit" curve. In FIG. 5, the curve is a parabola, one determines where there is a predetermined slope to the curve, and calculates the temperature of the ear drum 16.

An accelerometer that is believed to be useful in connection with the foregoing application is the ST LIS3L06AL three-axis linear accelerometer.

Figure 6:
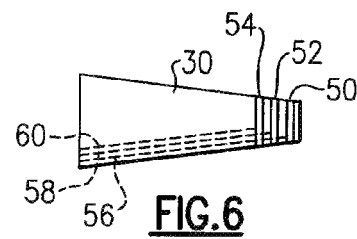
FIG. 6 is a side view illustration of the probe shown in FIG. 2 bearing three spaced, electrically-conductive rings, in accordance with another embodiment of the present invention.

Yet another embodiment of the present invention is depicted in FIG. 6. One or more electrical conductors may be disposed about the periphery of the probe 30. In FIG. 6, there are three such electrical conductors 50, 52, 54 in the shape of rings that are disposed about the small end of the probe 30 in a spaced relationship. In a preferred embodiment, the electrical conductors may be fashioned of flat copper tape approximately one-eighth inch wide, and the electrical conductors may be coated with a polyimide film marketed under the name "Kapton", which provides an insulating and protective function. Each of the conductors 50, 52, 54 may be connected via an associated wire 56, 58, 60, respectively, and disposed within the hollow probe 30 to the interior of the handle 32 of the thermometer 28.

An A/C waveform generator 62 is applied to each of the respective conductors 50, 52, 54. As each of the conductors 50, 52, 54 is brought into closer proximity to the walls of the ear canal 14, the capacitance of the electrical conductors 50, 52, 54 changes. Generally, if no object is near the electrical conductors 50, 52, 54, then no current flows through the conductors 50, 52, 54, but current increasingly flows as the electrical conductors 50, 52, 54 get closer to an object, such as the inner wall of the ear canal 14. The current flow in each of the conductors 50, 52, 54 is measured by a current meter 64. It is believed that an Omron B6T workbench demo board may be utilized for this purpose. When the current flowing in each of the conductors 50, 52, 54 has reached a certain predetermined threshold associated with that conductor, then the temperature reading can be associated with that probe location. The temperature selected as defining the temperature of the ear drum 16 may be the first temperature reading that occurs after such threshold condition has been satisfied or may be the highest temperature reading within a time interval after such threshold condition has been satisfied and continues to be satisfied. Again, referring to FIG. 7, a microprocessor 66 may obtain input from both the current meter 64 and the infrared-radiation detector 40 to assess whether the threshold conditions have been achieved, to obtain readings of the infrared radiation impinging upon the infrared-radiation detector 40, and to display the selected temperature on one or both of the displays 34, 36.

A particular algorithm that may be used for determining the temperature of the ear drum will now be described utilizing the probe 30 as shown in FIG. 6 and the capacitance sensor shown in FIG. 7. In connection with explaining the algorithm, it is helpful to have an understanding of how the structure of an ear typically affects its temperature. The outer pinna 12 of the ear is exposed to the ambient air and includes very little blood flow. Consequently, the temperature of the pinna 12 tends to be significantly affected by the ambient temperature, although where the human or other animal has been exercising, the pinna 12 may have a relatively elevated temperature. At the entrance of the ear canal 14, the temperature tends to be affected by the pinna 12, by the bony skull 68, which is still relatively cool, since it contains relatively little blood and is close to the external skin, and also by the relatively high-temperature brain, which is blood rich and possesses a relatively high temperature. Deep in the ear canal, the ear canal wall is relatively thin, and the temperature is affected primarily by the brain and by the ear drum 16, which indicates the core body temperature.

Figure 8A:
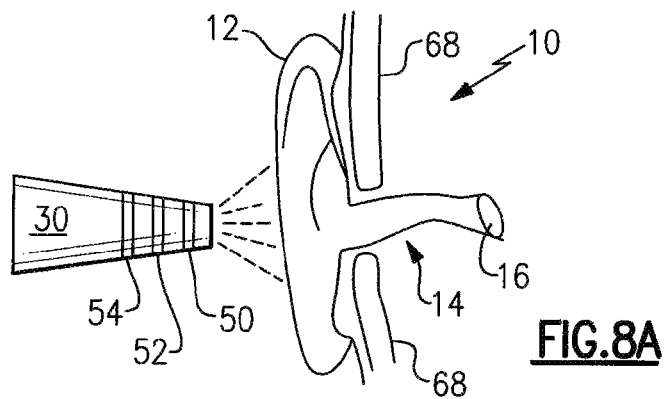
FIG. 8A is a schematic illustration of a probe with an infrared detector such as that shown in FIG. 6 approaching a human ear, with the dash lines indicating the field of "view" or sensing of the infrared detector.
Figure 8B:
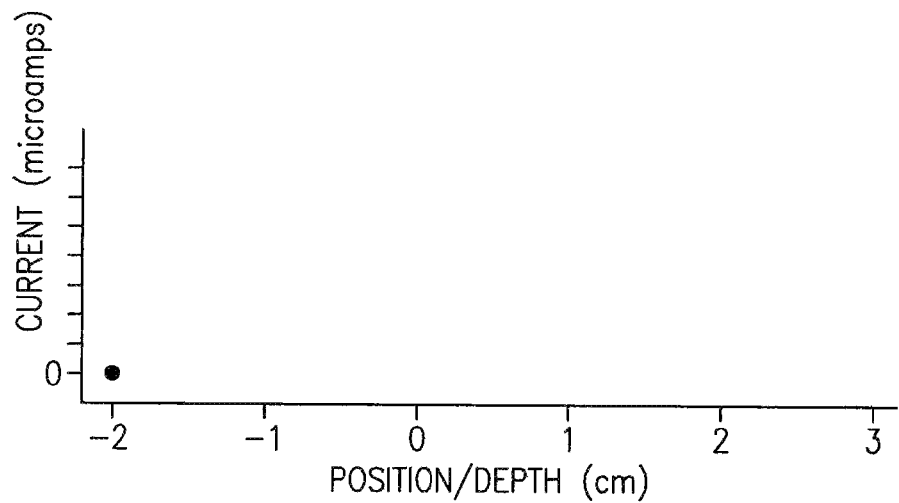
FIG. 8B is a graph indicating the current flowing through a capacitance sensor on the probe at a position relative to the ear canal.
Figure 8C:
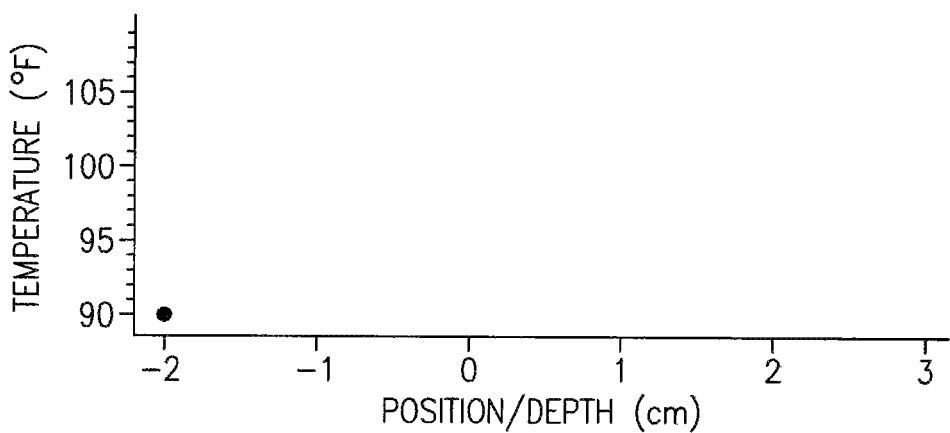
FIG. 8C is a graph indicating the corresponding temperature of the infrared radiation detected by the detector in the probe at a position relative to the ear canal.

As shown in FIG. 8A, when the probe 30 is positioned away from the pinna 12, the infrared detector in the probe 30 has a field of "view" or sensation of infrared radiation as depicted by the dash lines in FIG. 8A. The infrared detector senses and integrates infrared radiation emitted from objects in the entire field or view. Since the capacitance sensor on probe 30 is not in proximity to any animal tissue or other object, FIG. 8B shows the current flowing through the capacitance sensor will be zero. As shown in FIG. 8C, the amount of infrared radiation detected by the detector in the position shown in FIG. 8A will be greatly influenced by the ambient temperature, and in this example it is detected and correlated to be 90 degrees Fahrenheit.

Figure 9A:
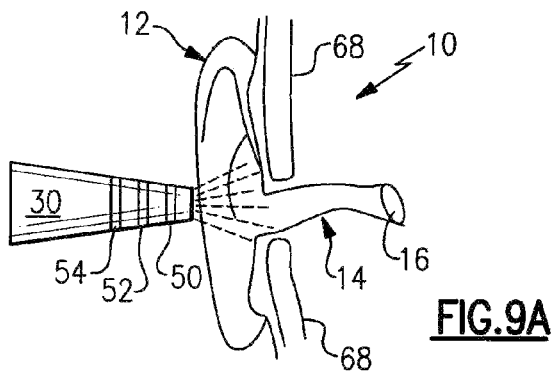
FIGS. 9A, 10A, 11A, and 12A illustrate the probe shown in FIG. 8A as it progresses toward and into the ear canal.
Figure 9B:
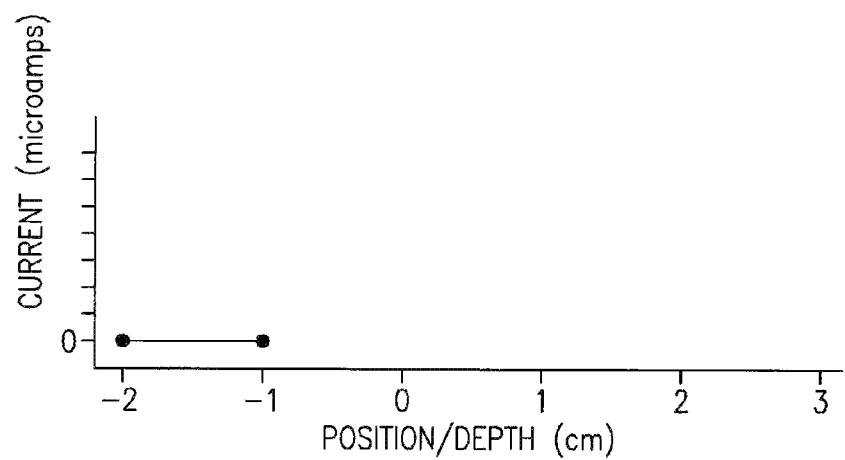
FIGS. 9B, 10B, 11B, and 12B are graphs corresponding to the graph in FIG. 8B and indicate the current flowing through the capacitance sensor as the probe is moved toward and enters into the ear canal.
Figure 9C:
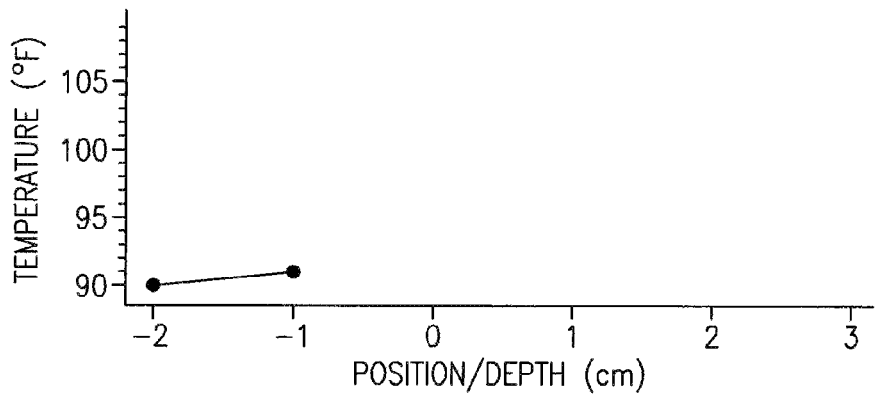
FIGS. 9C, 10C, 11C, and 12C are graphs corresponding to the graph in FIG. 8C and indicate the temperature corresponding to the infrared radiation detected by the probe as the probe is moved toward and enters into the ear canal.

As shown in FIG. 9A, the probe 30 is moved closer to the ear canal, but the current flowing through the capacitance sensor is still zero (FIG. 9B), and the temperature has risen only a single degree, to 91 degrees Fahrenheit (FIG. 9C).

Figure 10A:
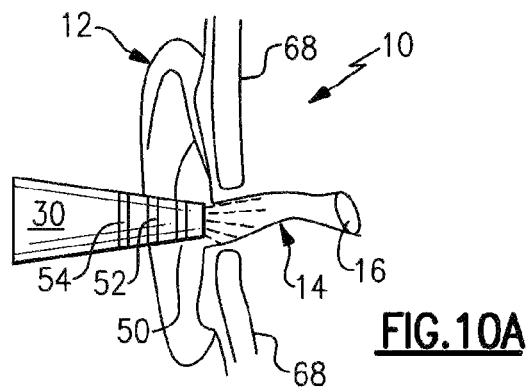
Figure 10B:
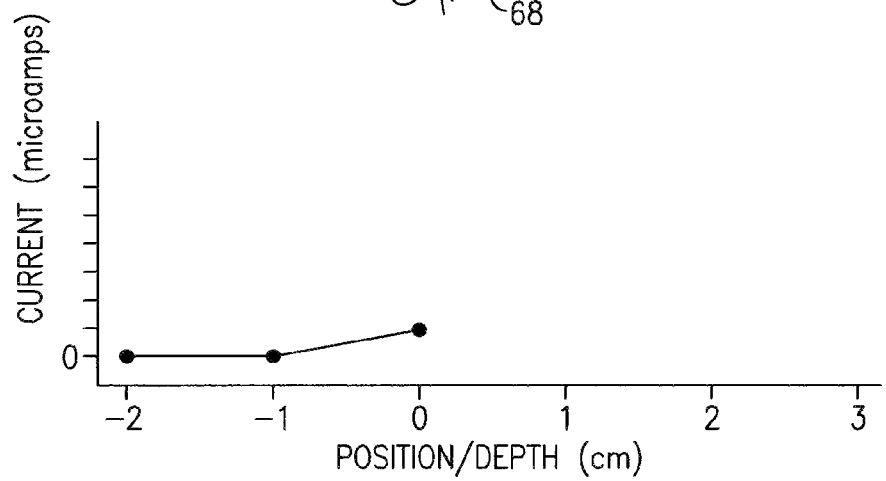
Figure 10C:
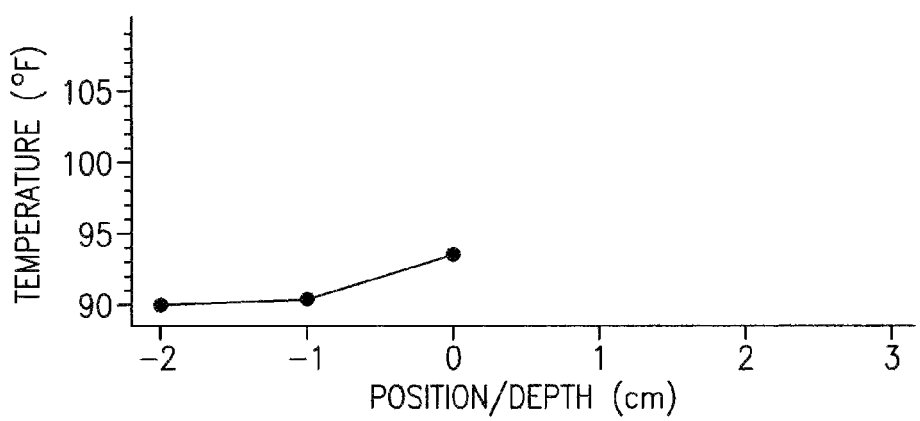

FIG. 10A depicts the small tip of the probe 30 exactly at the entrance of the ear canal 14. In this position, there will be a small current flow through the capacitance sensor, as indicated by FIG. 10B. Through empirical data testing of the probe 30 fitted with the capacitance sensor, the current flowing through the capacitance sensor where the probe tip is exactly at the entrance of the ear canal will be selected as a threshold current flow, and will define a so-called "zero" distance position relative to the ear canal 14. Similarly, other rates of current flow may be empirically tested and correlated with a distance of the tip of the probe 30 in the ear canal. As shown in FIG. 10C, the temperature detected by the probe 30 in the position shown in FIG. 10A has risen to 94 degrees Fahrenheit.

Figure 11A:
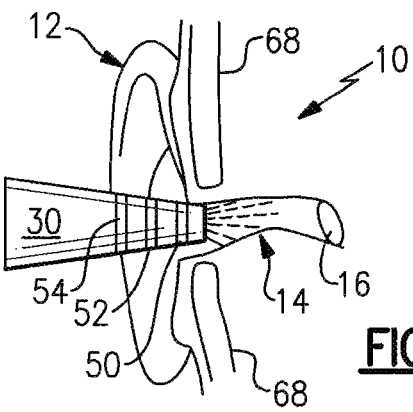
Figure 11B:
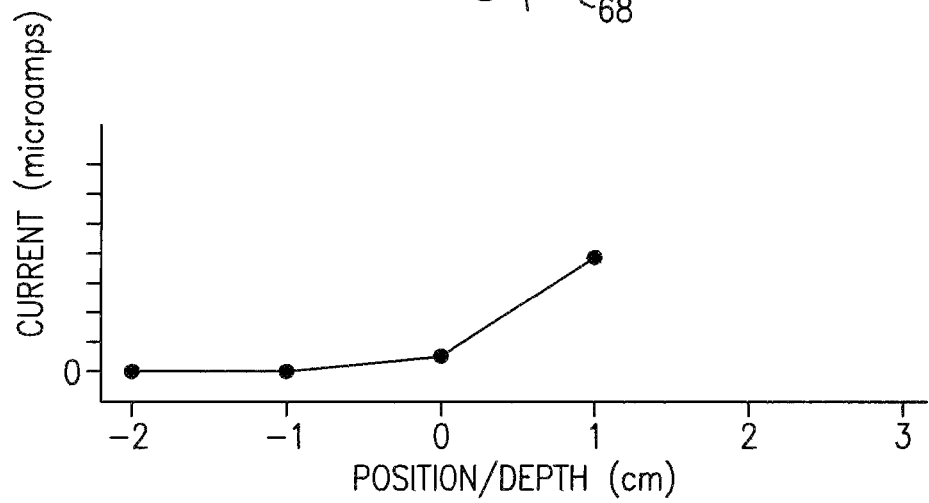
Figure 11C:
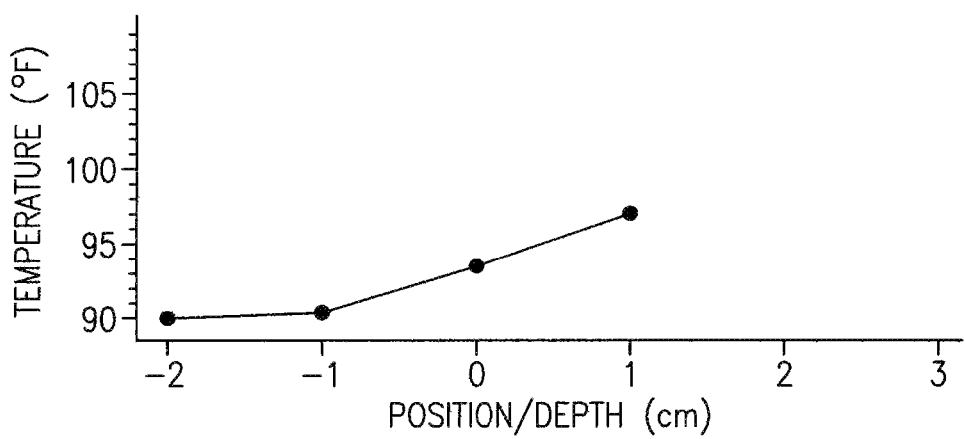

The tip of the probe 30 shown in FIG. 11A has been inserted a distance of one centimeter deep into the ear canal 14 from the entrance of the ear canal 14. As shown in FIG. 11B, the current flowing through the capacitance sensor has significantly increased because of the proximity of ear tissue to the capacitance sensor. As shown in FIG. 11C, the detected temperature has risen to 97 degrees Fahrenheit.

Figure 12A:
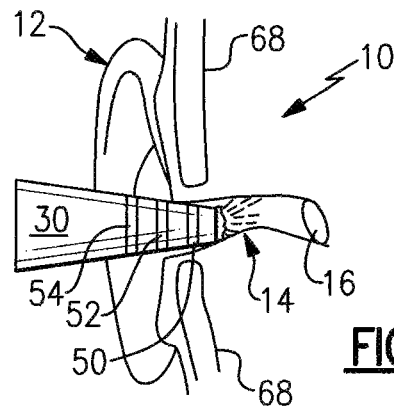
Figure 12B:
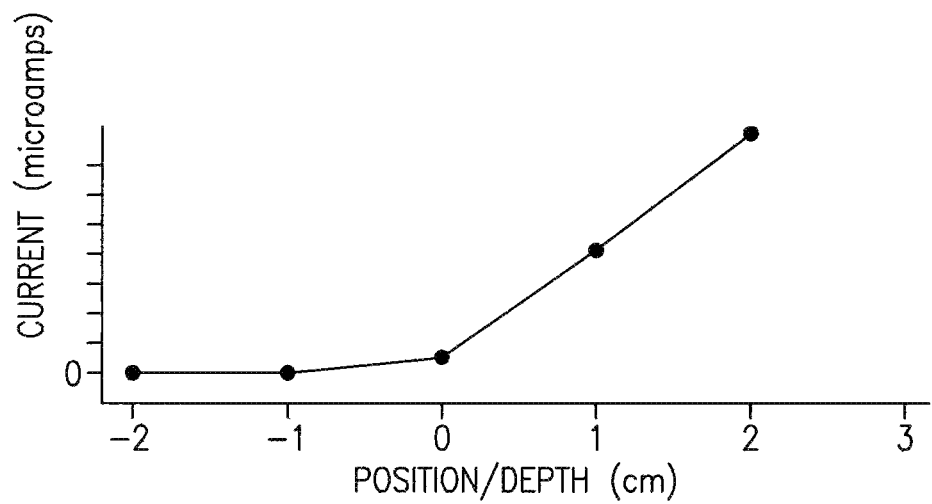
Figure 12C:
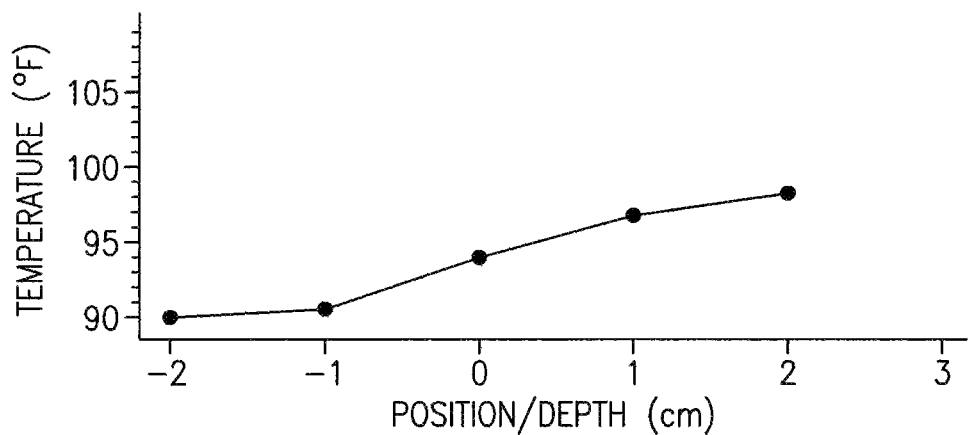

The position of the tip of the probe 30 shown in FIG. 12A is 2.0 centimeters into the ear canal 14 from the entrance to the ear canal 14. As shown in FIG. 12B, the current in the capacitance sensor has continued to rise. The temperature detected, as shown in FIG. 12C, has risen only slightly, to 98 degrees Fahrenheit.

Figure 14:
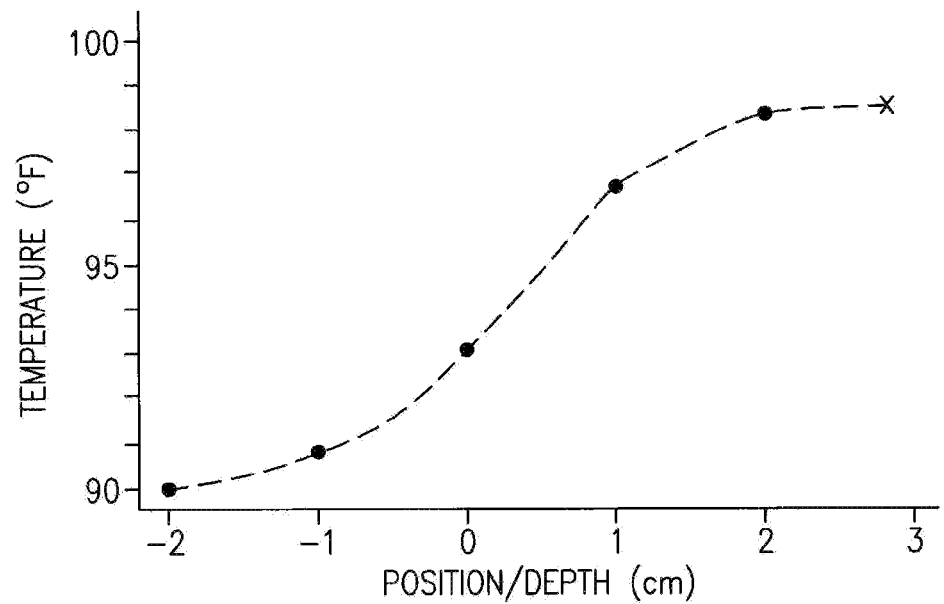
FIG. 14 is a graph indicating a typical curve of the temperature as sensed by the infrared detector as the detector approaches and enters into the ear canal.

FIG. 14 shows a typical plot of temperature detected by the infrared detector in the probe 30 where the "zero" distance indicates the entrance of the ear canal, where the ambient temperature around the pinna 12 is about 90 degrees Fahrenheit, and where the ear drum is 98.6 degrees Fahrenheit. Note that the slope of the plot is very shallow until about the position where the small tip of the probe 30 is at the entrance of the ear canal, then the slope is relatively steep from the "zero" position to about a one centimeter depth into the ear canal 14, and then the slope becomes very shallow at deeper penetrations into the ear canal beyond one centimeter.

Figure 13:
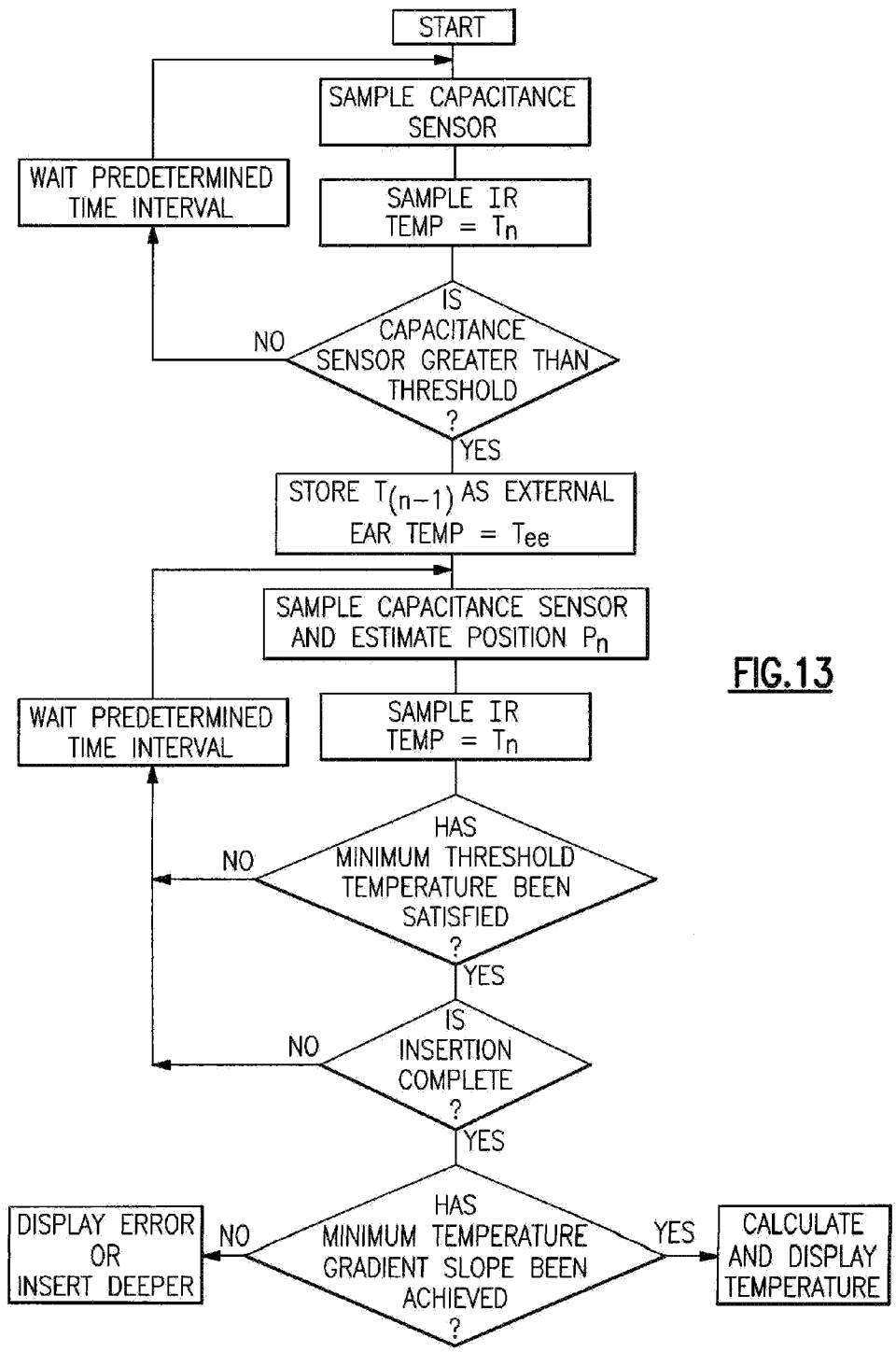
FIG. 13 is a flow chart indicating a sequence of how an estimate of the ear-drum temperature is determined in accordance with one embodiment of the present invention.

FIG. 13 shows a flow chart of sequences that can be used to determine an estimated temperature of the ear drum. The sequence may be started by depressing the push button 38, which initiates a sampling of the amperage flowing through the capacitance sensor. Such sampling may occur at essentially any rate, for example, ten samplings per second. The start also initiates a sampling of the amount of infrared radiation detected by the infrared-radiation detector, which may be correlated to a temperature. Again, the sampling may occur at essentially any rate, for example, ten samplings per second.

The sampling of the current flow through the capacitance sensor is analyzed to determine whether it has achieved the threshold current flow. If not, then a delay of a predetermined time interval, such as, for example, 100 milliseconds, occurs before the sampling of the current flow through the capacitance sensor and the sampling of the infrared radiation is re-initialized. If the current flow has achieved the threshold, then the temperature reading occurring when the threshold has been achieved is stored as the external ear temperature, $T_{EE}$.

Thereafter, the current flow of the capacitance sensor is continued to be sampled and an estimate of the position of the small tip of the probe 30 within the ear canal 14 is determined and the amount of infrared radiation, which correlates to a temperature, is also sampled corresponding to that particular position. The system may maintain a number of positions and temperature samplings, such as, for example, fifty samplings, with the first samplings being monitored, being the first samplings being discarded, as additional samplings are taken.

The system then determines whether a minimum threshold temperature, such as 93 degrees Fahrenheit, has been satisfied. If not, a delay of predetermined time interval, such as, for example, 100 milliseconds, occurs and then the sampling is repeated, while maintaining the same external ear temperature reading. If the minimum threshold temperature has been achieved, then a determination is made as to whether the insertion of the probe has been completed. Such a determination may be made either by depressing the push button 38 or by selecting a predetermined distance or estimated position of the probe 30 within the ear canal as determined by the current flow through the capacitance sensor. If the insertion is not complete, then again, a delay of a predetermined time interval, such as, for example, 100 milliseconds, occurs and the sampling is repeated, again, while maintaining the same external ear temperature reading. If the insertion is complete, then the system determines whether a minimum temperature change gradient, that is, a minimum slope of temperature versus distance has been achieved. In other words, the system determines whether, after achieving a minimum threshold temperature, a relatively shallow temperature slope, such as that shown in the region beyond one centimeter in FIG. 14, has been achieved. If such a minimum temperature gradient has not been achieved, then the system displays 34, 36 display a message such as "error" or "invalid" or "insert deeper" in the displays 34, 36. If the minimum threshold gradient has been achieved, then the system calculates an estimated ear drum temperature and displays that temperature on the displays 34, 36 according to the following algorithm:

$$T_{ED} = T_{ID} + ((T_{ID} - T_{EF}) \times a) + (dy/dx \times (B - ID))$$

where
- $T_{ID}$ is the infrared sensed temperature at the deepest point of insertion into the ear canal
- $T_{EE}$ is the temperature immediately external to the ear canal entrance
- a is a correction factor based upon empirical testing and should typically be on the order of one one-hundredth (0.01)
- dy/dx is the slope or gradient of the temperature rise at the deepest point of insertion into the ear canal
- ID is the deepest point of insertion into the ear canal from a point where the probe first enters the ear canal
- B is the ideal insertion depth (typically 2.0 cm for adults and 1.0 cm for a child)

It should be recognized here that the distance from the entrance of the ear canal 14 to the ear drum 16 varies from animal to animal, and among humans. For example, the length of the ear canal 14 in a human adult is about 2.6 centimeters and for a human child it is much shorter. Consequently, the algorithm should be customized for a particular animal or size of human. The current invention contemplates that the thermometer 28 may be provided with a switch on the handle 32 for changing the factor "B". For example, one position of the switch may indicate "under 2 years old" or "under 20 pounds", which switch position will cause the factor "B" to equal 1.0 centimeters. A second position of the switch will be indicated with a legend "3-9 years old" or "20-90 pounds" and will correspond to a "B" value of 1.5 centimeters, and a third position of the switch will be indicated with a legend "over 10 years old" or over 90 pounds", and will cause the "B" value to equal 2.0 centimeters.

It will be appreciated that the sequence shown in FIG. 13 and the above-recited formula or algorithm may be performed utilizing a microprocessor contained within the handle 32 of the thermometer 28.

Figure 15:
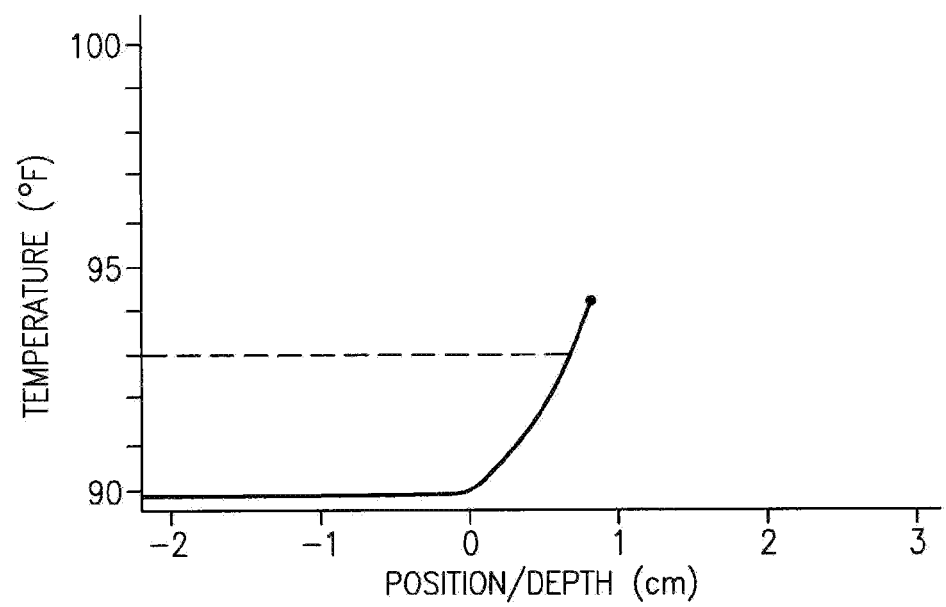
FIG. 15 is a graph of an attempted temperature reading taken when the probe is about 0.7 centimeters into the ear canal.

An example of how the sequence may operate will be demonstrated with reference to FIG. 15, which shows that prior to the probe 30 approaching the entrance of the ear canal 14, the infrared temperature reading was about 89.5 degrees Fahrenheit. At a distance of about 0.8 centimeters into the ear canal 14, the temperature has risen to about 94 degrees Fahrenheit. Even though a minimum threshold temperature, 93 degrees Fahrenheit, has been achieved, and even if the operator of the thermometer 28 believes that the insertion has been complete, such as by depressing the push button 38, the estimated temperature of the ear drum will not be calculated, but rather, a message such as "error" or "invalid" or "insert deeper" will be displayed on the displays 34, 36 because only a relatively steep temperature gradient has occurred after the minimum threshold temperature was achieved. Stated in other words, after the minimum threshold temperature was achieved, the slope of temperature versus distance has not sufficiently "flattened".

Figure 16:
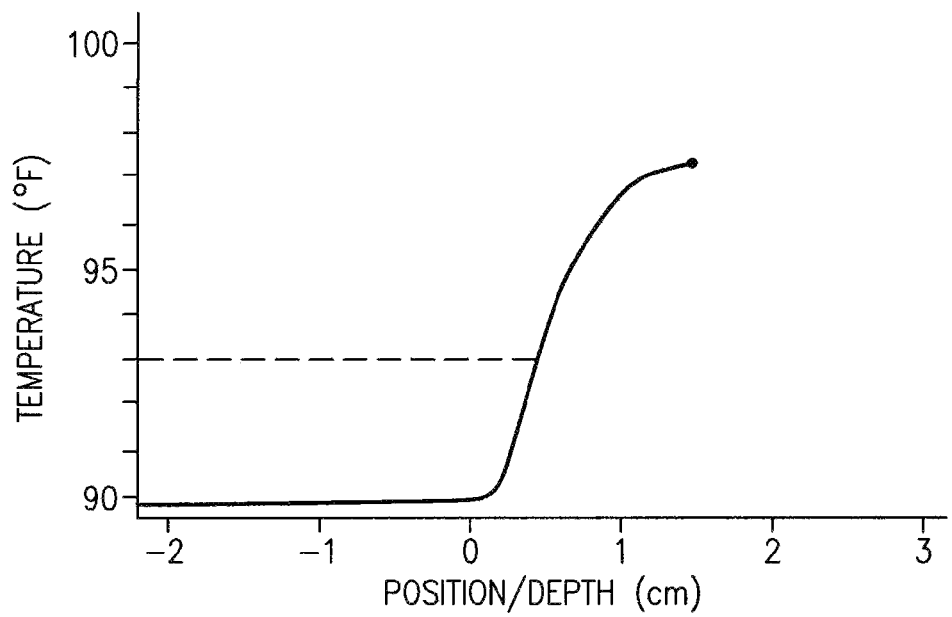
FIG. 16 is a graph of the temperature reading as the probe is about 1.3 centimeters into the ear canal.

FIG. 16 depicts an exemplary situation in which the insertion depth is 1.3 centimeters, at which point the infrared temperature reading is 97.5 degrees Fahrenheit, and the slope of the temperature gradient at that point is 1.4 degrees Fahrenheit per centimeter, and in which the external ear temperature at the "zero" point is 89.5 degrees Fahrenheit. When utilizing the following parameters set forth below with the above-reference formula or algorithm, the estimated ear drum temperature is 98.66 degrees Fahrenheit.

$T_{ID}$=97.5° F.
$T_{EE}$=89.5° F.
a=0.01
dy/dx=1.4° F./cm
ID=1.3 cm
B=2.0 cm $$T_{ED} = 97.5° \text{ F.} + ((97.5° \text{ F.} - 89.5° \text{ F.}) \times 0.01) +$$
$$(1.4° \text{ F./cm} \times (2.0 \text{ cm} - 1.3 \text{ cm}))$$
$$= 97.5° \text{ F.} + (0.08° \text{ F.}) + (0.98° \text{ F.})$$
$$= 98.66° \text{ F.}$$

Figure 17:
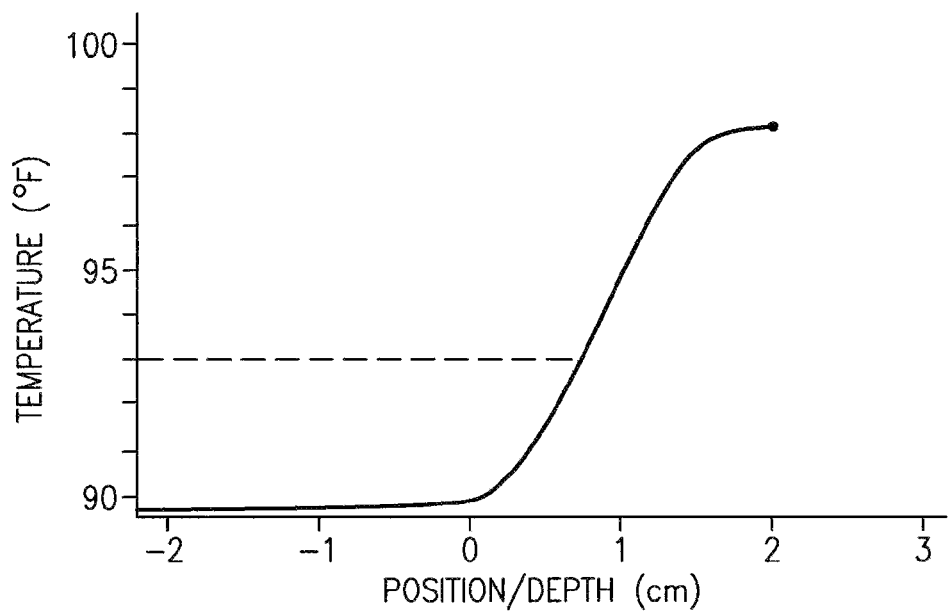
FIG. 17 is a graph of the temperature reading as the probe is about 2 centimeters into the ear canal.
Figure 18:
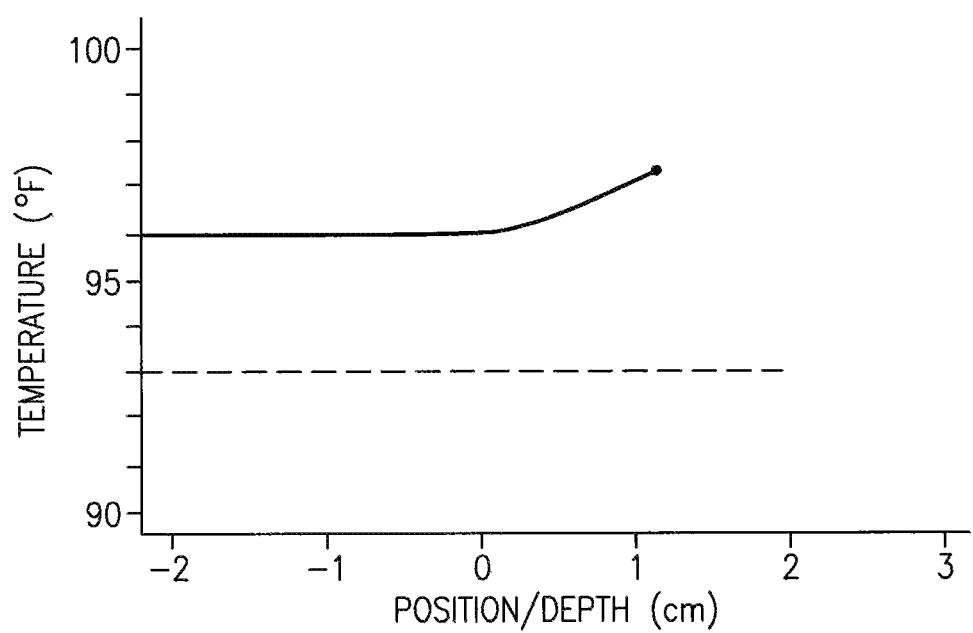
FIG. 18 is a graph of the temperature reading as the probe is inserted 1.0 centimeters into the ear canal, where the ambient temperature is relatively high.

Yet another example is depicted in FIG. 17, in which the insertion distance is 2.0 centimeters, the temperature gradient is 0.2 degrees Fahrenheit per centimeter, the temperature at the insertion depth is 98.5 degrees Fahrenheit, and the external ear temperature at point "zero" is 89.5 degrees Fahrenheit. When utilizing an "a" value of 0.01 and a "B" value of 2.0 centimeters and implementing the foregoing values in the aforementioned formula or algorithm, the estimated ear temperature is calculated as follows:

$$T_{ED} = 98.5° \text{ F.} + ((98.5° \text{ F.} - 89.5° \text{ F.}) \times 1.01) +$$
$$(0.2° \text{ F./cm} \times (2.0 \text{ cm} - 2.0 \text{ cm}))$$
$$= 98.5° \text{ F.} + (0.08° \text{ F.}) + (0° \text{ F.})$$
$$= 98.58° \text{ F.}$$

From the foregoing, it will be appreciated that a microprocessor may be operationally connected to the infrared detector and to the capacitance sensor circuitry and to the push button 38 to received data that may be utilized in the sequence shown in FIG. 13 and that may be applied in accordance with the foregoing formula or algorithm to determine an estimation of the ear drum temperature.

The invention also contemplates that the same sort of process could be used during the withdrawal of the probe 30 from the ear canal in order to verify the accuracy of the data obtained during the insertion of the probe 30 into the ear canal. If the data obtained during withdrawal is different by more than a predetermined amount or ratio from the data obtained during insertion, then the ear drum temperature estimate may be declared suspect or invalid, and the operator may be urged or required to repeat the entire process.

As an optional feature, the probe 30 itself may be pre-heated to a select temperature, such as 90 degrees Fahrenheit, so that the temperature of the probe 30 itself will not have any significant effect on modifying the temperature of nearby tissue; otherwise, a relatively cold probe 30 might have a possible effect on the amount of infrared radiation emitted by such tissue. Such pre-heating may be achieved by placing any resistor-like material on the probe 30 and selectively applying an electric current from a battery located within the handle 32 of the thermometer 28 such as by selectively activating a switch located on the handle 32. The thermometer 28 could also be provided with a light indicator that emits light when the probe 30 is sufficiently pre-heated and ready for use. Such a light might be activated either after a pre-selected time or after another thermometer located in the probe 30 determines that the pre-selected temperature has been achieved.

Figure 7:
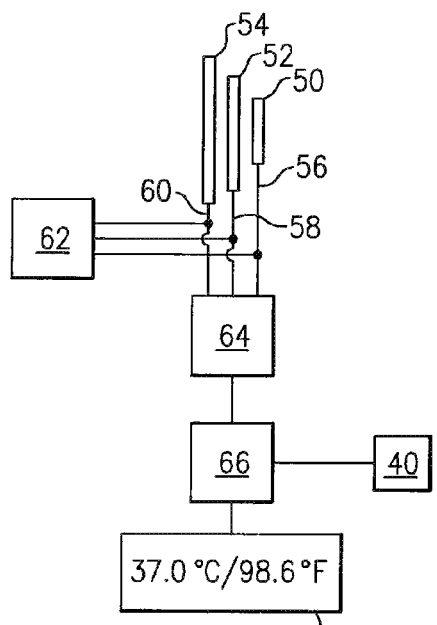
FIG. 7 is a schematic block diagram of the thermometer in accordance with the present invention utilizing the probe shown in FIG. 5.

The present invention further contemplates various embodiments utilizing one or more electrical conductors in addition to those embodiments shown in FIGS. 6 and 7. For example, FIG. 6 discloses a series of three electrical conductors 50, 52, 54 in the shape of rings circumferentially disposed about the small end of the probe 30 in a spaced relationship. Each of the rings is connected via an electrical conductor wire 56, 58, 60 to A/C waveform generator 62 and via current meter 64 to a microprocessor 66. Several other, additional embodiments utilizing electrical conductors may be especially useful assessing not only the depth of insertion of the probe 30 into the ear canal, but also the orientation of the probe 30 within the ear canal.

Figure 19:
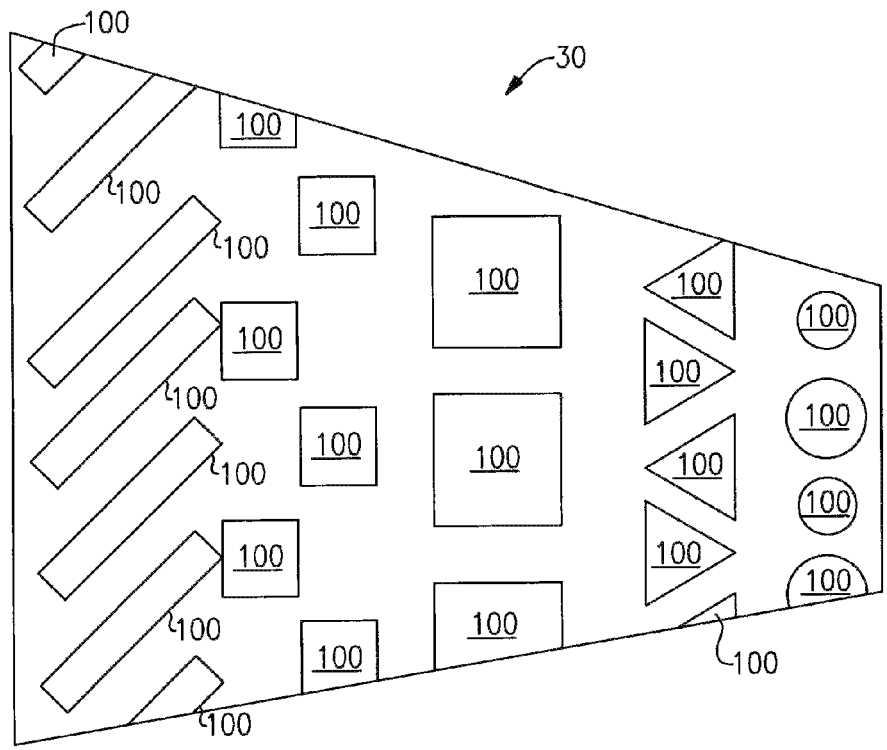
FIG. 19 is a side view illustration of the probe shown in FIG. 2 bearing a variety of different electrode pads disposed in various arrays, in accordance with yet another embodiment of the present invention.

The probe 30 may be provided with a variety of capacitive proximity sensors comprising electrode pads 100 disposed about the outer periphery of the probe 30. The electrode pads 100 may be fashioned in a variety of shapes, sizes, and arrays. For example, as shown in FIG. 19, the electrode pads 100 adjacent to the smaller end of the probe 30 comprise a series of circular electrode pads 100 or ranged circumferentially about the probe 30, with electrode pads 100 having alternately larger and smaller circular diameters. Adjacent to the series of circular electrode pads 100 is a series of triangular-shaped electrode pads 100 circumferentially arranged about the probe 30, with the triangles pointing in alternatively different longitudinal directions. In the center of the probe 30 is a series of electrode pads 100 having a square profile circumferentially arranged about the periphery of the probe 30. Also as shown in FIG. 19, a series of staggered electrode pads 100 is shown in which each electrode pad 100 possesses the shape of a square, and each electrode pad 100 is alternately closer or farther away from the smaller end of the probe 30. The electrode pads 100 as shown adjacent to the large end of the probe 30 each possess a rectangular configuration, and extend obliquely about the periphery of the probe 30. Each of the rectangular-shaped electrode pads 100 in this series is alternately longer or shorter than adjacent electrode pads 100. The sizes and shapes of the pads may be selected, for example, to adapt to the conventional, normal contours of the ear canal when the probe is satisfactorily inserted into the ear canal.

The electrode pads 100 are connected via thin electrical wires or tracers (not shown) that electrically connect each electrode pad 100 to electrical apparatus, such as a waveform generator, a current meter, and a microprocessor. When the probe 30 is inserted into the ear canal, the conductivity/capacitance of each electrode pad 100 will change depending upon the proximity of the ear canal to the associated electrode pad 100. A microprocessor can be programmed to set a predetermined threshold value of the conductivity/capacitance of each electrode pad 100 that must be satisfied in order to determine that an appropriate temperature reading can be obtained. The threshold settings may be determined differently for each electrode pad 100, or may be set at the same value for groupings of electrode pads. For example, the threshold values for the electrode pads 100 disposed closest to the smaller end of the probe 30 may be relatively high, and the threshold values of the electrode pads 100 toward the larger end of the probe 30 may be set relatively low.

The microprocessor may also be programmed to require that the threshold values for each one of the electrode pads 100 must be satisfied in order for a proper temperature reading to be obtained. Alternatively, the microprocessor may be programmed to require that a certain percentage of the threshold values be satisfied, or that an aggregate value of conductivity/capacitance be obtained, in order for a proper temperature reading to be obtained. Further, the microprocessor can be programmed so as to require that a particular grouping of electrode pads 100 each attains a threshold value, that a percentage of electrode pads 100 in such grouping attain a threshold value, or that the aggregate value of conductivity/capacitance for such grouping achieve a threshold value, in order for a proper temperature reading to be obtained.

Figure 20:
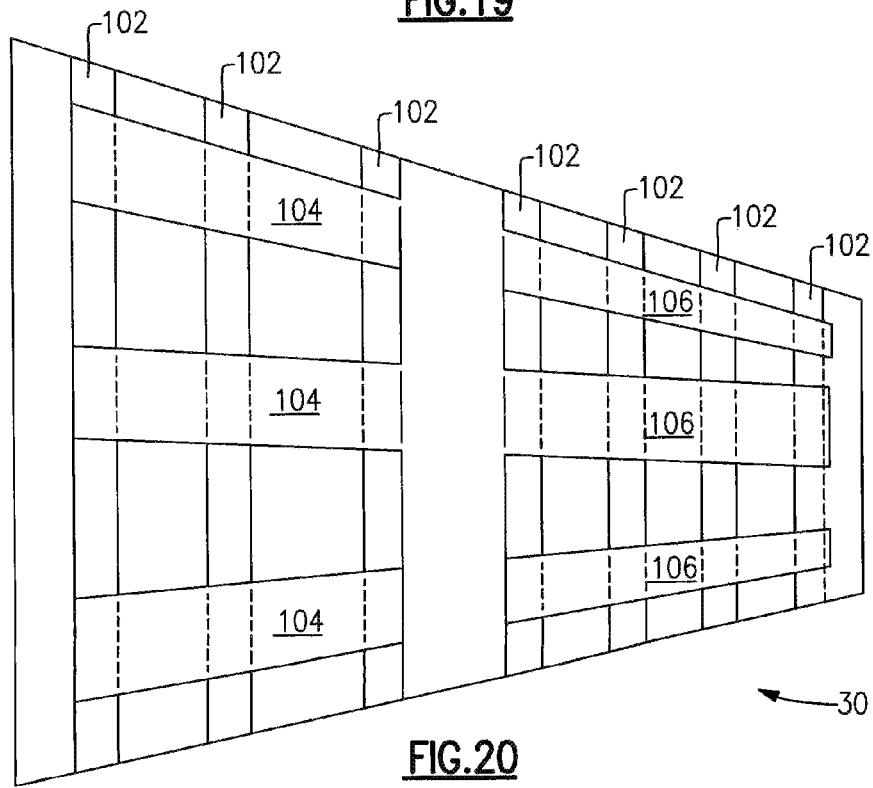
FIG. 20 is a side view illustration of the probe shown in FIG. 2 bearing a series of longitudinally extending, spaced electrode pads overlapping a series of circumferentially extending, spaced electrode pads, in accordance with still another embodiment of the present invention.

There shown in FIG. 20 yet another embodiment of the present invention in which a series of electrically conductive rings 102 extends circumferentially about the periphery of the probe 30. Each of the rings 102 may be fashioned of the same thickness and width, and may be equidistantly spaced from adjacent rings 102. The probe 30 shown in FIG. 20 also possesses a series of longitudinally extending electrically conductive strips that are each bifurcated into two sections 104, 106. The strip sections 104, 106 are disposed over the rings 102. It will be appreciated that, in the embodiment shown in FIG. 20, the rings 102 and the strip sections 104, 106 are essentially electrode pads, and that such pads overlap each other to varying degrees. When such electrode pads are in close proximity to each other, especially in an overlapping relationship, the electrode pads may create electric field interference due to capacitive coupling, which results in skewed conductive/capacitance readings and assessments for the associated electrode pads. Accordingly, the present invention contemplates that the electric current applied to each electrode pad, such as the rings 102 and the strip sections 104, 106, may be applied in an alternating fashion so that when the conductivity/capacitance of the rings 102 is being monitored, the electric current is not applied to the strip sections 104, 106, and when the electric current is applied to the strip sections 104, 106, the electric current is not applied to the rings 102. Such alternating application of electric current to different electrode pads may occur extremely quickly, on the order of a millisecond. It should also be appreciated that instead of altering the electric current to different groupings of electrode pads, the electric current may be applied to any one or more electrode pads in accordance with any preselected sequence. When the electric current is so applied, then a conductivity/capacitance reading for the electrode pads to which electric current is applied may be determined without a risk of electric field interference.

Figure 21:
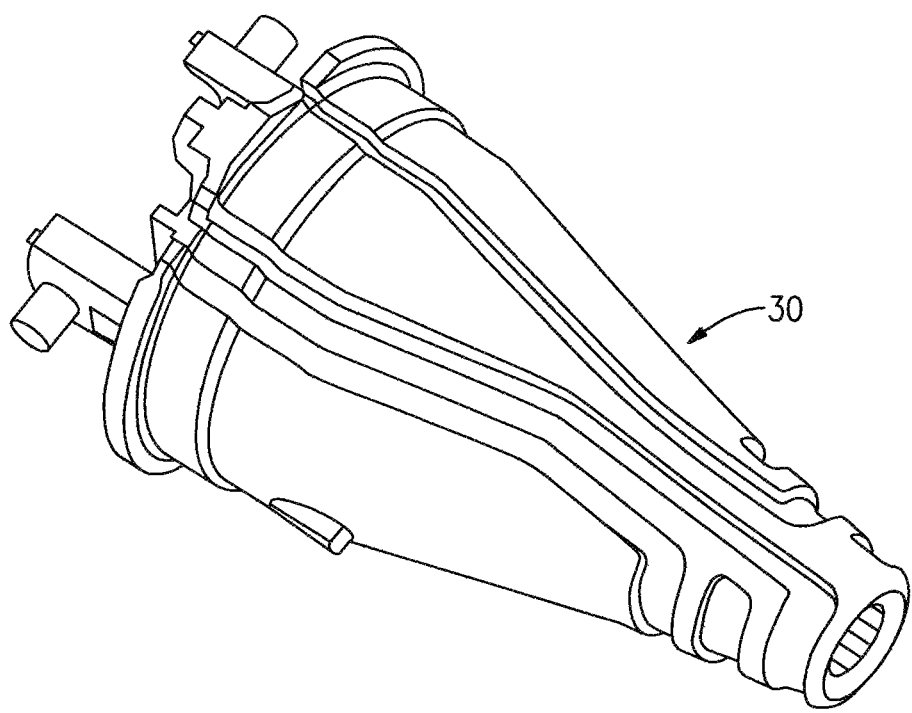
FIG. 21 is a perspective illustration of the probe shown in FIG. 2 integrally formed with a plurality of channels on the peripheral surface thereof and adapted to receive electrode pads and conductive tracer lines, in accordance with another embodiment of the present invention.

There shown in FIG. 21 a probe 30 in accordance with yet another embodiment of the present invention. The probe 30 shown in FIG. 21 possesses a peripheral surface in which a series of channels 108, depressions, or other voids has been etched or integrally formed with the probe 30. The channels 108 may be filled with a variety of electrically conductive materials, such as a an electrically conductive elastomer, for example, conductive elastomers sold under the trade name "Chomerics", an electrically conductive epoxy, or an electrically conductive plating material. A protective coating may be applied to cover the material disposed in the channels 108. As such, the conductive material in the channels 108 forms both the electrode pads and the tracer lines.

It should be appreciated that probe 30 shown in FIG. 21 may instead comprise a cap or cover for a conventional probe, which cover may be mounted over a conventional probe by means of a snap-fit connection, by adhesive, or by frictional engagement. In such a retrofit embodiment, the cover and the thermometer are provided with cooperative electrical transmission elements so that a microprocessor may assess when the cover is properly mounted and so that electric current/capacitance in the conductive rings, pads, bands, channels, or zones of the cover may be generated and analyzed. In one embodiment, the cover possesses the electrical conductive/capacitance elements, and cooperative electrical contact elements are provided on the probe and on the cover such that when the cover is properly mounted over the probe the cover contact element physically abuts the probe contact element, thereby facilitating electrical communication between the thermometer and the cover. In another embodiment, the cover is provided with an electric power source such as a tiny embedded battery, electrical analysis circuitry, a microprocessor, and an antenna by which information can be transmitted wirelessly to and from the thermometer.

Figure 22:
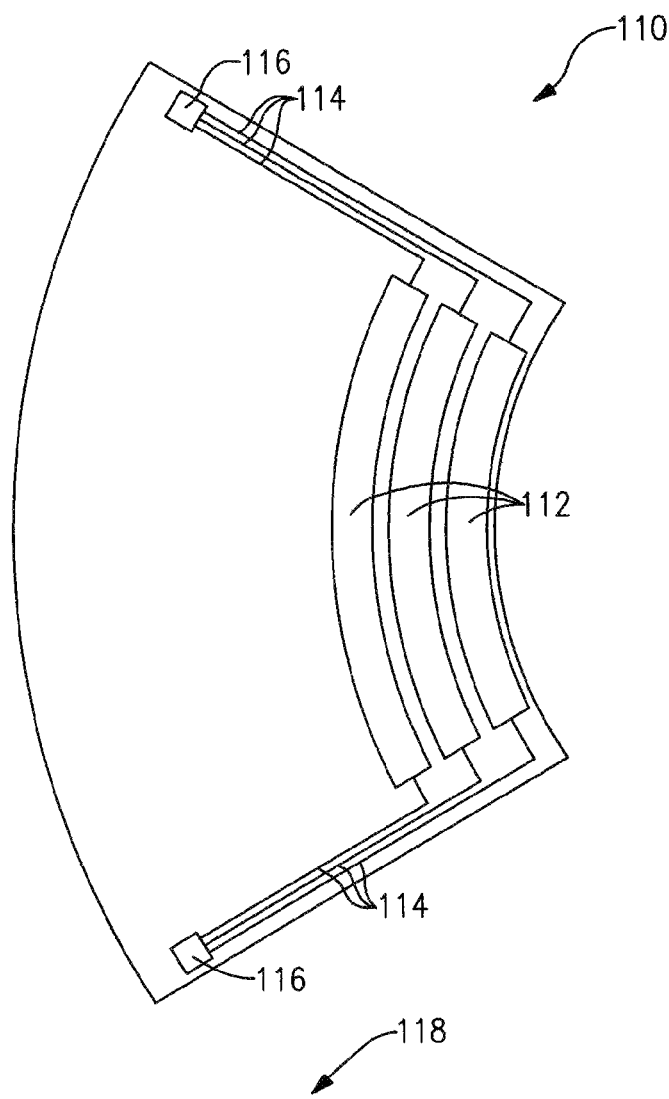
FIG. 22 is a plan view of a sheet of material containing electrode pads, conductive tracer lines, and microchips adapted to be conformingly wrapped around the periphery of the probe shown in FIG. 2, in accordance with yet another embodiment of the present invention.

There shown in FIG. 22 yet another embodiment of the present invention, which includes a sheet 110 of material adapted to be disposed about and against the periphery of the probe 30. The sheet 110 includes a series of three arcuate, curved, electrically conductive bands 112. When the sheet 110 is wrapped around the periphery of the probe 30, the bands 112 generally circumferentially extend about the probe 30, near the smaller end thereof. Each end of an electrically conductively band 112 is connected via a tracer line 114 to an associated microchip 116. In a preferred embodiment, the bands 112 each have a width of about 2.7 millimeters, and each band 112 is spaced about 1.0 millimeter from an adjacent band 112. Also preferably, each tracer line is on the order of about 0.007 inches wide, and is spaced from adjacent tracer lines by a distance of about 1 millimeter. In the embodiment shown in FIG. 22, the bands 112 and the tracer lines 114 may be formed of a conductive ink or conductive paint.

It will be appreciated that the sheet shown in FIG. 22 may be applied in a retrofit manner on a conventional probe. The microchips 116 are designed to provide communication with a microprocessor that may be employed also as a retrofit in association with the IR thermometer. In such an embodiment, a microprocessor and the microchips 116 are designed to communicate with each other. The microchips 116 may include RFID technology that will help identify the characteristics of the sheet 110 applied to the conventional probe and also as an indication that the sheet 110 has been applied to the conventional probe. Likewise, when the probe shown in FIG. 21 is in the form of a retrofit cap or cover, a microchip may be mounted thereon for a similar function. Suitable microchips are the MPRO3X and the MPR121 sensor controllers manufactured and offered by Freescale Semiconductor, Inc.

The sheet 110 may be selectively secured to a conventional probe by an adhesive. The invention contemplates that the sheet 110, in addition to being sized and shaped for particular conventional probes having different peripheral configurations, may also be imprinted with information to the effect that it is compatible with certain brands or types of conventional probes.

Although the use of conductive inks and conductive paints has been described with reference to the embodiment shown in FIG. 22, it should be appreciated that conductive inks and conductive paints may be used in other embodiments of the present invention. The various embodiments may also employ etched metal foil and metal plating as the electrical conductive elements.

The microprocessor may also be programmed with an algorithm that assigns a weighting factor to the conductivity/capacitance of each electrode pad in evaluating whether the probe 30 is inserted properly within the ear canal for a temperature reading to be taken. For example, if the conductivity/capacitance of one electrode pad has attained a threshold, then the microprocessor assigns a value of two points for that condition; if conductivity/capacitance of another electrode pad has attained such a threshold, then a value of one point is assigned for that condition; and if the conductivity/capacitance of still another electrode pad has not attained such a threshold, then a value of minus eight points is assigned for that condition. The microprocessor then sums the values and if the sum exceeds a predetermined number, then the microprocessor will indicate that the probe 30 has been inserted properly for a temperature reading to be taken or may simply permit a temperature reading to be taken. If the sum does not exceed the predetermined number, then the microprocessor will indicate that the probe 30 has been improperly positioned or may simply prevent a temperature reading from being taken.

The microprocessor may be programmed with an algorithm that evaluates the conductivity/capacitance values of each electrode pad and then determines the orientation and depth of insertion of the probe 30 relative to the ear canal. The microprocessor may then be programmed to evaluate how the orientation or depth of insertion should be changed in order to achieve a proper orientation and depth for taking a temperature reading, that is, how the probe 30 should be moved in order to achieve a conductivity/capacitance condition for the electrode pads that satisfies the predetermined standard for properly taking a temperature reading. The microprocessor may also be programmed to adjust or correct a temperature reading if the orientation and the depth of the probe is not optimal. In this latter embodiment, empirical studies may be conducted to determine the discrepancies between the true core body temperature and the temperature read by the thermometer when the probe is disposed at various non-ideal positions and then the data from such studies may be used to compile profiles or algorithms for correcting the temperature read by the thermometer.

Figure 23:
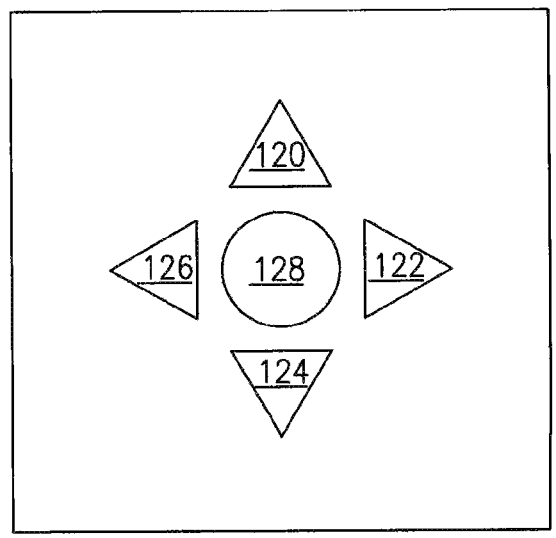
FIG. 23 is a schematic illustration of a visual display that may be used for instructing the operator of the thermometer whether to change the orientation or depth of the thermometer probe in the ear canal.

The present invention permits an evaluation of whether both a satisfactory orientation and a satisfactory depth of insertion of the probe has been attained for a proper IR temperature reading to be taken. As shown in FIG. 23 the thermometer may also include a visual display 118 operatively connected to a power source and the microprocessor for providing a visual guide for inserting the probe 30 into the ear canal. The display may, for example, include four radially extending, equiangularly projecting LEDs 120, 122, 124, 126 in the shape of arrows extending about a large central, circular LED 128. The microprocessor may indicate that the probe 30 needs to be moved in a particular direction (left/right/up/down) by lighting one or more of the arrow-shaped LEDs 120, 122, 124, 126 or needs to be inserted deeper by lighting the centrally disposed, circular LED 128. The microprocessor may indicate that the probe 30 has been properly positioned in the ear canal for a temperature reading to be taken by blinking or flashing all of the LEDs, for example. Alternatively, the visual display may comprise a screen on which textual instructions appear. Instead of visual indications, the thermometer may be equipped with a speaker operatively connected to a power source and to the microprocessor whereby audio instructions may be provided such as "Move the probe to the left" or "Insert deeper." or "Correct position. Temperature can now be taken."

Although the proximity sensors have been particularly described as being electrically conductive rings, pads, bands, or channels, the invention broadly contemplates that the physical structure of the proximity sensors may be more varied and that the proximity sensors may be broadly described as electrically sensing points, zones, areas, or regions that are not dependant on the particular physical structure of the sensing element.

While exemplary embodiments have been presented in the foregoing description of the invention, it should be appreciated that a vast number of variations within the scope of the invention may exist including other methods of determining probe insertion positioning. The foregoing examples are not intended to limit the nature or the scope of the invention in any way. Rather, the foregoing detailed description provides those skilled in the art with a foundation for implementing other exemplary embodiments of the invention.

We claim:

1. A thermometer for determining a temperature of a vertebrate animal's ear drum disposed at the inner end of the animal's ear canal defined by an ear canal wall, said thermometer comprising:
    a probe adapted to be inserted into the ear canal, said probe possessing a substantially frusto-conical configuration about a substantially longitudinal axis and possessing an outer peripheral surface;
    a detector adapted to sense infrared radiation emitted by the ear canal and the ear drum, said detector being operatively coupled to said probe;
    an array of at least three electrically conductive zones disposed adjacent to and arranged about said outer peripheral surface;
    at least one electrode overlapping at least one of said zones;
    at least one sensor electrically connected to each of said zones and also electrically connected to said at least one electrode, said at least one sensor adapted to sense the conductivity of each of said zones as said probe is inserted into the ear canal and adapted to sense the conductivity of said at least one electrode as said probe is inserted into the ear canal; and
    a microprocessor configured to assess the orientation of the longitudinal axis of said probe relative to the wall of said ear canal in the vicinity of said probe at least partially based on the conductivity sensed by said at least one sensor.

2. The thermometer according to claim 1 wherein each of said at least three zones comprises an electrode pad, wherein the microprocessor is configured to assess the conductivity relative to a threshold value associated with each of said at least three zones, wherein the microprocessor is configured to assign a weighting value to each of said assessments, and wherein the microprocessor is configured to inhibit the temperature from being determined at least partially based on said assessments and said assignments.

3. The thermometer according to claim 1 wherein each of said at least three zones comprises an electrode pad, wherein the microprocessor is configured to assess the conductivity relative to a threshold value associated with each of said at least three zones, and wherein the microprocessor is configured to inhibit the temperature from being determined unless at least one of said assessments attains at least one predetermined condition.

4. The thermometer according to claim 1 wherein the microprocessor is in operative electrical communication with said at least one sensor and configured to assess the conductivity of each of said zones.

5. The thermometer according to claim 1 wherein the microprocessor is configured to assess whether the aggregate conductivity of each of said zones exceeds a predetermined value.

6. The thermometer according to claim 1 wherein the microprocessor is configured to assess whether the conductivity of a preselected percentage greater than zero percent of the number of said zones exceeds a predetermined value.

7. The thermometer according to claim 1 wherein said outer peripheral surface is formed with a plurality of surface depressions in which each of said zones are situated.

8. The thermometer according to claim 1 further comprising an adapter configured and adapted to be selectively mounted over said probe and wherein said zones are carried by said adapter.

9. The thermometer according to claim 1 wherein said at least one electrode extends substantially longitudinally along said probe.

10. The thermometer according to claim 1 further comprising a source of electric charge operatively connected to each of said zones and said at least one electrode, said source adapted to apply an electric charge according to a preselected sequence among said zones and said at least one electrode.

11. A thermometer for determining a temperature of a vertebrate animal's ear drum disposed at the inner end of the animal's ear canal defined by an ear canal wall, said thermometer comprising:
    a probe adapted to be inserted into the ear canal, said probe possessing a substantially frusto-conical configuration about a substantially longitudinal axis and possessing an outer peripheral surface;
    a detector adapted to sense infrared radiation emitted by the ear canal and the ear drum, said detector being operatively coupled to said probe;
    an array of at least three electrically conductive zones disposed adjacent to and arranged about said outer peripheral surface, wherein said zones are mounted on a flexible sheet disposed substantially conformingly against said outer peripheral surface;
    at least one sensor electrically connected to each of said zones, said at least one sensor adapted to sense the conductivity of each of said zones as said probe is inserted into the ear canal; and
    a microprocessor configured to assess the orientation of the longitudinal axis of said probe relative to the wall of said ear canal in the vicinity of said probe at least partially based on the conductivity sensed by said at least one sensor.

* * * * *